(12) United States Patent
Nicolaides et al.

(10) Patent No.: US 7,106,446 B2
(45) Date of Patent: Sep. 12, 2006

(54) MODULATED REFLECTANCE MEASUREMENT SYSTEM WITH MULTIPLE WAVELENGTHS

(75) Inventors: Lena Nicolaides, Castro Valley, CA (US); Jeffrey T. Fanton, Los Altos, CA (US); Alex Salnik, Castro Valley, CA (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 425 days.

(21) Appl. No.: 10/439,455

(22) Filed: May 16, 2003

(65) Prior Publication Data

US 2003/0234932 A1    Dec. 25, 2003

Related U.S. Application Data

(60) Provisional application No. 60/390,487, filed on Jun. 21, 2002.

(51) Int. Cl.
*G01N 21/55* (2006.01)

(52) U.S. Cl. ....................................... 356/445

(58) Field of Classification Search ........ 356/445–448, 356/237.1–237.5, 72
See application file for complete search history.

(56) References Cited

U.S. PATENT DOCUMENTS

| | | | |
|---|---|---|---|
| 4,634,290 A | 1/1987 | Rosencwaig et al. | 374/5 |
| 4,636,088 A | 1/1987 | Rosencwaig et al. | 374/5 |
| 4,854,710 A | 8/1989 | Opsal et al. | 356/432 |
| 5,074,669 A | 12/1991 | Opsal | 356/445 |
| 5,206,710 A | 4/1993 | Geiler et al. | 356/432 |
| 5,293,215 A | 3/1994 | Pfendler et al. | 356/360 |

(Continued)

OTHER PUBLICATIONS

S. Holé et al., POSTER entitled "Wavelength Multiplexed Photoreflectance for submicronic thermal imaging," *12 ICPPP, Toronto, Jun. 24-27, 2002*, Jun. 2002, 1 page in length.

S. Holé et al., "Wavelength multiplexed photoreflectance for submicronic thermal imaging," *12 ICPPP, Toronto, Jun. 24-27, 2002* (Book of Abstracts), Jun. 2002, p. 125.

G. Tessier et al., "Quantitative thermal imaging by synchronous thermoreflectance with optimized illumination wavelengths," *Applied Physics Letters*, vol. 78, No. 16, Apr. 16, 2001, pp. 2267-2269.

S. Holé et al., "Submicronic thermal imaging by wavelength multiplexed photoreflectance technique," *Electronic Letters*, vol. 38, No. 17, Aug. 15th, 2002, pp. 986-987.

*Primary Examiner*—Michael P. Stafira
(74) *Attorney, Agent, or Firm*—Stallman & Pollock LLP

(57) ABSTRACT

A modulated reflectance measurement system includes three monochromatic diode-based lasers. Each laser can operate as a probe beam or as a pump beam source. The laser outputs are redirected using a series of mirrors and beam splitters to reach an objective lens. The objective lens focuses the laser outputs on a sample. Reflected energy returns through objective and is redirected by a beam splitter to a detector. A lock-in amplifier converts the output of the detector to produce quadrature (Q) and in-phase (I) signals for analysis. A Processor uses the Q and/or I signals to analyze the sample. By changing the number of lasers used as pump or probe beam sources, the measurement system can be optimized to measure a range of different samples types.

18 Claims, 2 Drawing Sheets

U.S. PATENT DOCUMENTS

| | | | |
|---|---|---|---|
| 5,408,327 A | 4/1995 | Geiler et al. | 356/432 |
| 5,741,070 A | 4/1998 | Moslehi | 374/161 |
| 5,978,074 A * | 11/1999 | Opsal et al. | 356/72 |
| 5,982,499 A * | 11/1999 | Chichester et al. | 356/445 |
| 6,049,220 A | 4/2000 | Borden et al. | 324/765 |
| 6,081,127 A | 6/2000 | Wagner et al. | 324/765 |
| 6,151,522 A * | 11/2000 | Alfano et al. | 600/473 |
| 6,323,951 B1 | 11/2001 | Borden et al. | 356/502 |

* cited by examiner

MODULATED REFLECTANCE MEASUREMENT SYSTEM WITH MULTIPLE WAVELENGTHS

PRIORITY CLAIM

The present application claims priority to U.S. Provisional Patent Application Ser. No. 60/390,487, filed Jun. 21, 2002, the disclosure of which is incorporated herein by reference.

TECHNICAL FIELD

The subject invention relates generally to optical methods for inspecting and analyzing semiconductor wafers and other samples. In particular, the subject invention relates to methods for increasing the accuracy and flexibility of systems that use modulated optical reflectivity to analyze semiconductor wafers.

BACKGROUND OF THE INVENTION

There is a great need in the semiconductor industry for metrology equipment that can provide high resolution, non-destructive evaluation of product wafers as they pass through various fabrication stages. In recent years, a number of products have been developed for the nondestructive evaluation of semiconductor samples. One such product has been successfully marketed by the assignee herein under the trademark Therma-Probe. This device incorporates technology described in the following U.S. Pat. Nos. 4,634,290; 4,646,088; 5,854,710; 5,074,669 and 5,978,074. Each of these patents is incorporated in this document by reference.

In the basic device described in the patents, an intensity modulated pump laser beam is focused on the surface of a sample for periodically exciting the sample. In the case of a semiconductor, thermal and plasma waves are generated in the sample that spread out from the pump beam spot. These waves reflect and scatter off various features and interact with various regions within the sample in a way that alters the flow of heat and/or plasma from the pump beam spot.

The presence of the thermal and plasma waves has a direct effect on the reflectivity at the surface of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be investigated.

In the basic device, a second laser is provided for generating a probe beam of radiation. This probe beam is focused colinearly with the pump beam and reflects off the sample. A photodetector is provided for monitoring the power of reflected probe beam. The photodetector generates an output signal that is proportional to the reflected power of the probe beam and is therefore indicative of the varying optical reflectivity of the sample surface.

The output signal from the photodetector is filtered to isolate the changes that are synchronous with the pump beam modulation frequency. In the preferred embodiment, a lock-in detector is used to monitor the magnitude and phase of the periodic reflectivity signal. This output signal is conventionally referred to as the modulated optical reflectivity (MOR) of the sample.

In the early commercial embodiments of the Therma-Probe device, the pump and probe laser beams were generated by gas discharge lasers. Specifically, an argon-ion laser emitting a wavelength of 488 nm was used as the pump source. A helium neon laser operating at 633 nm was used as the probe source. More recently, solid-state laser diodes have been used and are generally more reliable and have a longer lifetime than the gas discharge lasers. In the current commercial embodiment, the pump laser operates at 780 nm while the probe laser operates at 670 nm.

In practice, the response of the sample to the pump beam is dependent to some degree on the wavelength. Further, the sensitivity of the system is also dependent on either pump or probe beam wavelength and the relationship between the pump and probe beam wavelengths. The combination of wavelengths selected by the assignee in its commercial embodiment is intended to strike a balance allowing measurements over a relatively broad range of samples. However, it can be shown that certain samples could be more accurately measured if the pump and probe beam wavelengths were optimized for that sample type or sample range.

In the most common commercial application of the Therma-Probe, the density or dosage levels of implants in silicon are measured. While the current pump and probe beam wavelengths provide good sensitivity across a relatively wide range of doses, certain regions are less sensitive than others. Accordingly, it would be a benefit if the user was permitted to select a particular set of wavelengths to perform certain measurements.

SUMMARY

The present invention provides a modulated reflectance measurement system with multi-wavelength measurement capability. For one implementation, the measurement system includes three monochromatic diode-based or diode-pumped semiconductor lasers. Each laser can operate as a probe beam source or as a pump beam source. The laser outputs are redirected using a series of mirrors and beam splitters to reach an objective lens. The objective lens focuses the laser outputs on a sample. Reflected energy returns through objective and is redirected by a beam splitter to a detector. A filter prepares the outputs of the detector for analysis by a processor. Typically, the filter includes a lock-in amplifier that converts the output of the detector to produce quadrature (Q) and in-phase (I) signals for analysis. The processor typically converts the Q and I signals to amplitude and/or phase values to analyze the sample. In other cases, the Q and I signals are used directly.

The use of three different lasers provides six possible combinations where a single probe beam is used with a single pump beam. Alternately, two lasers can be used to produce different probe beams while the third laser produces the pump beam. In another variation, two lasers can produce pump beams (at different modulation frequencies) while the third produces a probe beam. Another configuration uses all three lasers to produce intensity modulated pump beams. The light reflected by the sample originating from the first laser is monitored at the difference between the modulation frequencies of the second and third lasers. The reflected light of the second and third lasers is monitored in an analogous fashion. In this way, the present invention provides a dynamically reconfigurable measurement system that can be optimized to measure a range of different sample types.

For another implementation, the measurement system includes a pump laser and a probe laser. One or both of these lasers are wavelength tunable. The pump laser and probe lasers are controlled by a modulator. The laser outputs are redirected using a series of mirrors and beam splitters to reach an objective lens. The objective lens focuses the laser outputs on a sample. Reflected energy returns through objective and is redirected by a beam splitter to a detector. A filter prepares the outputs of the detector for analysis by a processor. Typically, the filter includes a lock-in amplifier that converts the output of the detector to produce quadrature (Q) and in-phase (I) signals for analysis. The processor typically converts the Q and I signals to amplitude and/or phase values to analyze the sample. In other cases, the Q and I signals are used directly. By selectively controlling the wavelengths produced by the pump laser and/or probe laser, the operation of modulated reflectance measurement system can be optimized to measure a range of different sample types.

For another implementation, of the measurement system pump and probe lasers are added as modular subsystems. Typically, this includes separate low-dose, mid-dose, high-dose, and all-dose modules. Each of these modules includes a pump laser and a probe laser having wavelengths that are selected to optimally analyze a particular range of implantation dosages. The all-dose module is intended to provide a wideband tool that operates over a range of dosage levels. The low-dose module, mid-dose module, and high-dose module provide insight into discrete portions of that range. The modules share a set of common components, which typically include optics, a detector and a processor. By selectively enabling or disabling the modules (alone or in combination), the operation of the operation of modulated reflectance measurement system can be optimized to measure a range of different sample types.

DETAILED DESCRIPTION OF THE PREFERRED EMBODIMENTS

Figure 1:
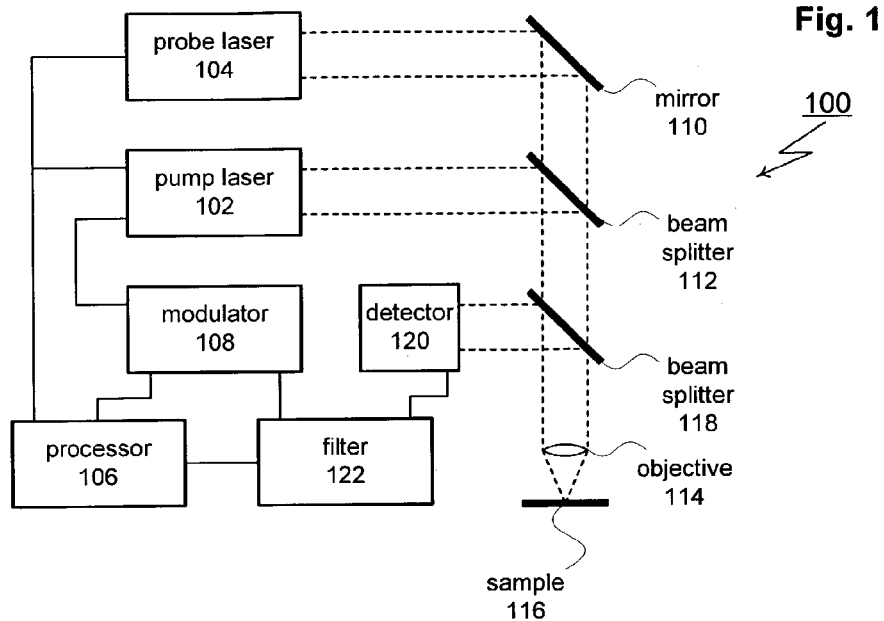
FIG. 1 is a block diagram of a modulated reflectance measurement system that uses two wavelength tunable laser sources.

The present invention provides a modulated reflectance measurement system with multi-wavelength measurement capability. In FIG. 1, one possible implementation for this system is shown and generally designated 100. As shown in FIG. 1, modulated reflectance measurement system 100 includes a pump laser 102 and a probe laser 104. At least one, and for some implementations both, of these lasers are wavelength tunable. Preferably, the output can be tuned over a range of at least 50 nm. Pump laser 102 and probe laser 104 are controlled by a processor 106. The time varying characteristics of the output of pump laser 102 are controlled by a modulator 108.

The output of pump laser 102 and probe laser 104 are redirected by a mirror 110 and a beam splitter 112, respectively. After being redirected, the two outputs pass through an objective lens 114 and are focused on a sample 116. The reflected energy returns through the objective 114 and is redirected by a beam splitter 118 towards a detector 120. Detector 120 measures the energy reflected by sample 116 and forwards a corresponding signal to a filter 122. Filter 122 includes a lock-in amplifier that uses the output of detector, along with the output of modulator 108 to produce quadrature (Q) and in-phase (I) signals for analysis. Processor 106 typically converts the Q and I signals to amplitude and/or phase values to analyze the sample. In other cases, the Q and I signals are used directly. By selectively controlling the wavelengths produced by pump laser 102 and/or probe laser 104, the operation of modulated reflectance measurement system 100 may be optimized to match the characteristics of sample 116.

Figure 2:
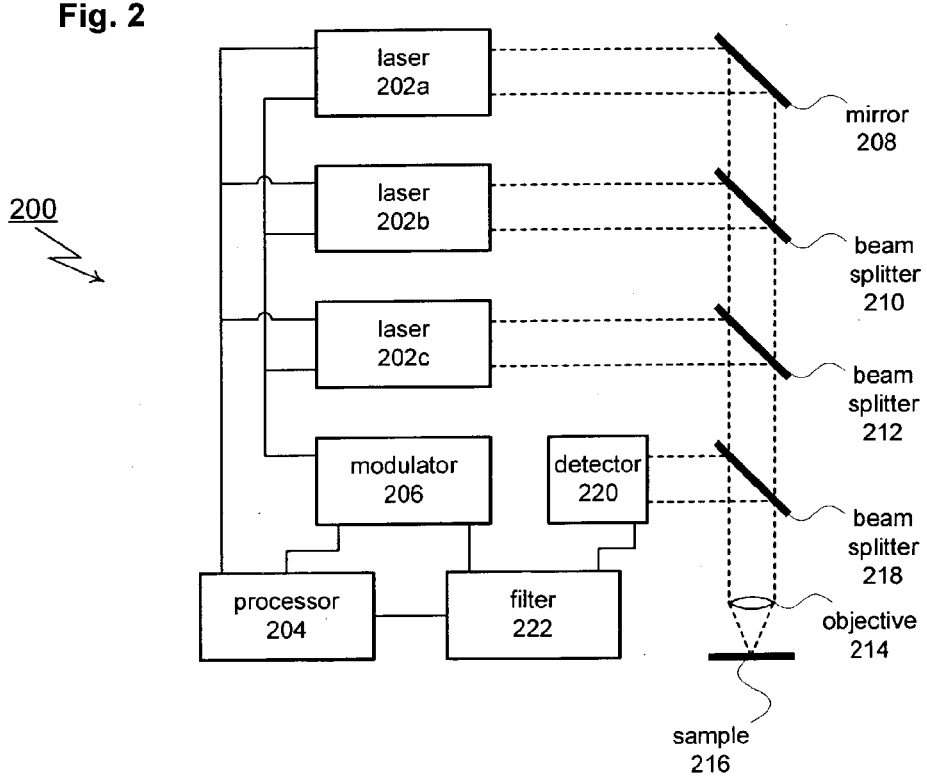
FIG. 2 is a block diagram of a modulated reflectance measurement system that uses three single wavelength laser sources.

In FIG. 2, a second possible implementation for the modulated reflectance measurement system is shown and generally designated 200. In FIG. 2, modulated reflectance measurement system 200 includes three lasers 202a through 202c. Each laser 202 is typically monochromatic and each laser 202 typically operates at a different spectrum. Lasers 202 are generally diode-based or diode-pumped semiconductor lasers. Solid-state laser diodes are available that have outputs throughout the entire visible spectrum as well as in the infrared and near UV. Lasers 202 are controlled by a processor 204 and a modulator 206. Each laser 202 is controlled independently allowing processor 204 to enable or disable any of lasers 204. Lasers 204 that are enabled may be configured to produce intensity-modulated outputs or configured to produce non-modulated (i.e., constant intensity) outputs.

The output of lasers 202a, 202b, and 202c are redirected by a mirror 208, a beam splitter 210 and a beam splitter 212, respectively. After being redirected, the outputs pass through an objective lens 214 and are focused on a sample 216. The reflected energy returns through the objective 214 and is redirected by a beam splitter 218 towards a detector 220. Detector 220 measures the energy reflected by sample 216 and forwards a corresponding signal to a filter 222. Filter 222 typically includes a lock-in amplifier that uses the output of detector, along with the output of modulator 206 to produce quadrature (Q) and in-phase (I) signals for analysis. Processor 204 typically converts the Q and I signals to amplitude and/or phase values to analyze the sample. In other cases, the Q and I signals are used directly.

A number of different configurations are available to control the operation of lasers 202. These configurations include a single pump single probe configuration where pump and probe beams are generated by respective lasers 202. A multiple probe, single pump configuration is also supported where two lasers 202 generate probe beams with the remaining laser 202 generating a pump beam. Similarly, a multiple pump, single probe configuration is supported where two lasers 202 generate pump beams with the remaining laser 202 generating a probe beam. A multiple pump, multiple probe configuration is also available where all three lasers 202 generate intensity-modulated beams.

For the single pump single probe configuration, processor 204 chooses one or more of lasers 202 to produce a pump beam and one or more of lasers 202 to produce a probe beam. The lasers selected to produce the pump beam are controlled by modulator 206 to have a time varying output. In the simplest case, one of lasers 202 provides the pump beam while one of lasers 202 provides the probe beam. Since each laser 202 is typically configured to operate at a different wavelength, there are six possible combinations of different pump and probe beams. This allows modulated reflectance measurement system 200 to be configured to analyze a range of samples having different characteristics.

For the multiple probe, single pump configuration, modulated reflectance measurement system 200 is configured to include two lasers 202 that provide the probe beam and one laser 202 provides the pump beam. Since reflectance may be wavelength dependent, probing at multiple wavelengths can be used to enhance the information obtained for some sample types. Since lasers 202 are fully interchangeable between pump and probe duties there are three different configurations that include two probe lasers 202. This allows the multiple probe, single pump configuration to analyze a range of different samples types.

For the multiple pump, single probe configuration, two lasers 202 provide the pump beam while the remaining laser 202 provides the probe beam. Since different wavelengths of light produce different thermal and plasma effects within sample 216, pumping at multiple wavelengths can be used to enhance the information obtained for some sample types. Since lasers 202 are fully interchangeable between pump and probe duties there are three different configurations that include two pump lasers 202. This allows the multiple pump configuration, single probe to analyze a range of different samples types.

When the multiple pump, single probe configuration is used, the lasers 202 selected to produce the pump beam are controlled by modulator 206 to have a time varying output. In such cases, different modulations will typically be used to produce the different pump beams. It is also possible to measure (either alternatively or in addition) the reflected light of either of the two pump beams. Based on the optical heterodyne technique as discussed in U.S. Pat. No. 5,206,710, either pump beam could monitored as a probe beam For the multiple pump, multiple probe configuration, all three lasers 202 generate intensity modulated beams, each at a different modulation frequency. The light reflected by the sample originating from laser 202a is monitored at the difference between the frequencies with respect to both lasers 202b and 202c. Light reflected by the sample originating from laser 202b is monitored at the difference between the frequencies with respect to lasers 202a and 202c. Similarly, light reflected by the sample originating from laser 202c is monitored at the difference frequencies with respect to lasers 202b and 202a. Thus, three lasers 202 gives the possibility of simultaneous measurement at three different probe beam wavelengths, each at two different pump beam wavelengths.

The different configurations provide a flexible mechanism for optimizing modulated reflectance measurement system 200 to analyze a range of different samples types. This is particularly true where a range of different density or dosage levels must be measured for different semiconductor wafers. It is also beneficial when analyzing ultra shallow junctions and other semiconductor features.

In general, it should be appreciated that the particular combination of components shown in FIG. 2 is intended to be representative in nature—a wide range of alternative configurations are possible. For example, as shown in FIG. 2 the optical path in modulated reflectance measurement system 200 is largely defined by a series of beam splitters 210, 212, 218 and a mirror 208. The selection of particular splitter or mirrors is governed by the wavelengths. With appropriate coatings, the beam splitters 210, 212, 218 can be fixed in position. However, it is also possible to move the mirrors into and out of the beam paths to control the propagation direction of the light. It is also possible to use shutters to control light propagation. It should also be appreciated that the use of three lasers 202 is only an example. The same techniques can be extended to support any number of lasers.

In another embodiment, only two lasers 202a and 202b, each having a different wavelength output, are provided. The output of either or both the laser can be intensity modulated. The user can select which of the two beams are monitored.

In one configuration, laser 202a acts as the pump and laser 202b acts as the probe. In another configuration, laser 202a acts as the probe and laser 202b acts as the pump. Both lasers can be modulated and either could act as the probe by monitoring the different frequency. The user can select the appropriate configuration based on the type of sample being measured. In order to obtain a reasonable amount of additional information, the wavelength separation between the two lasers should be at least 50 nm and preferably 100 nm or more.

Figure 3:
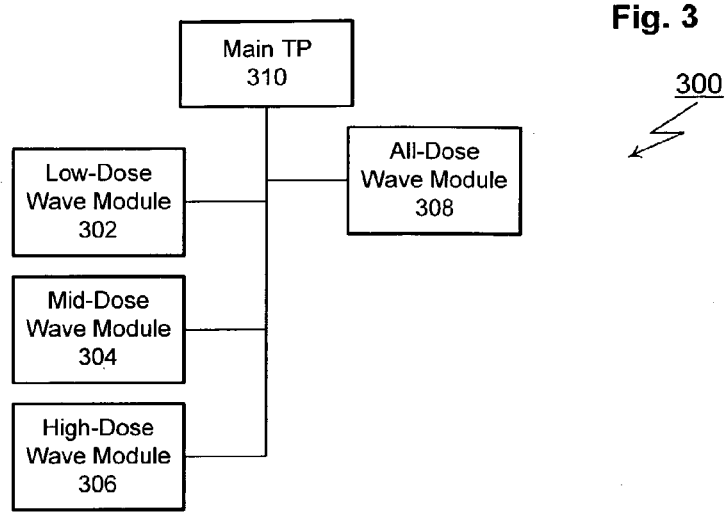
FIG. 3 is a schematic diagram of a modulated reflectance measurement system that uses four modular laser sources.

In FIG. 3, a third possible implementation for the modulated reflectance measurement system is shown and generally designated 300. For this implementation, pump and probe lasers are added as modular subsystems. FIG. 3 shows four of these modular subsystems. In order, they are: a low-dose module 302, a mid-dose module 304, a high-dose module 306, and an all-dose module 308. Each of these modules includes a pump laser and a probe laser having wavelengths that are selected to optimally analyze a particular range of implantation dosages. The all-dose module 308 is intended to provide a wideband tool that operates over a range of dosage levels. Low-dose module 302, mid-dose module 304, and high-dose module 306 provide insight into discrete portions of that range. Each of these modules uses a set of common components (e.g.: optics, filter, processor) designated 310 in FIG. 3.

For the example of FIG. 3, the different modules are intended to analyze different implantation dosage ranges. It should be appreciated that this is a representative implementation. Modules could also be selected to analyze other features, such as a range of modules designed to analyze different ultra shallow junctions.

Figure 4:
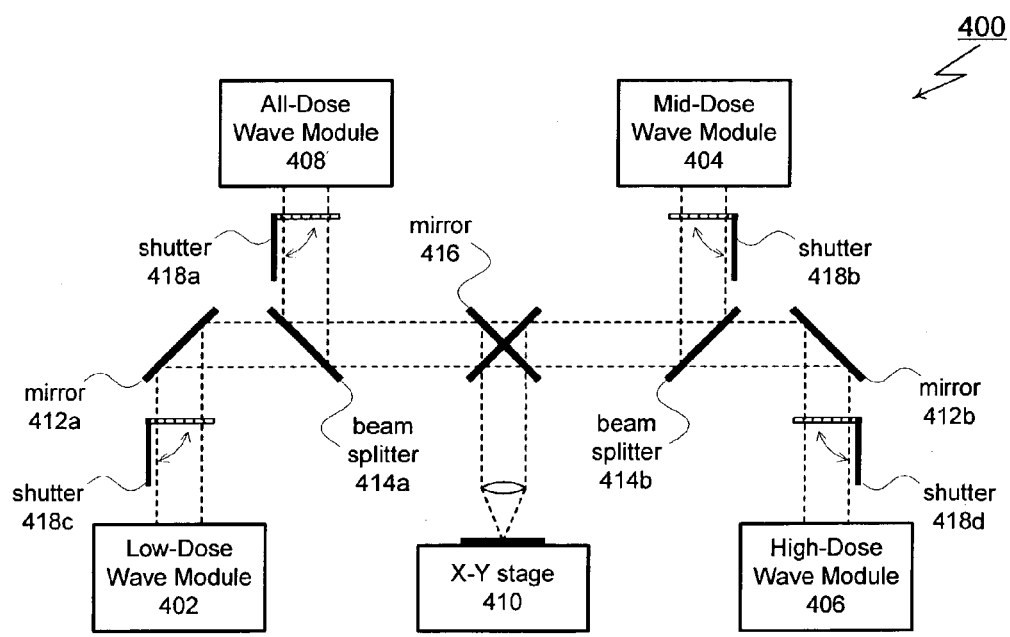
FIG. 4 is a block diagram of an implementation of the modulated reflectance measurement system of FIG. 3.

FIG. 4 shows a modulated reflectance measurement system 400 implemented using the modular approach. System 400 includes a low-dose module 402, a mid-dose module 404, a high-dose module 406, and an all-dose module 408 (or, equivalently different modules for different ultra shallow junctions). An X-Y stage 410 that allows relative positioning for a sample is shared by each of the modules. The optical path within modulated reflectance measurement system 400 is defined by mirrors 412a, 412b and beam splitters 414a and 414b. A rotating mirror 416 selects the module (or modules) that have access to X-Y stage 410 and sample at any given time A series of shutters 418a through 418d controls optical propagation within modulated reflectance measurement system 400. For example, if high-dose 406 module is used, shutters 418a through 418c block the beams from low-dose module 402, a mid-dose module 404, and all-dose module 408.

The separate modules shown in FIGS. 3 and 4 may also be used in parallel to produce multiple pump or multiple probe beams. To support the use of multiple probe beams, beam splitters 414a and 414b are implemented using a suitable dichroic design. As discussed previously, reflectance may be wavelength dependent. As a result probing at multiple wavelengths can be used to enhance the information obtained for some sample types. Multiple pump beams are typically accommodated using different modulation frequencies. Since different wavelengths of light produce different thermal and plasma effects, pumping at multiple wavelengths can be used to enhance the information obtained for some sample types. The modular approach provides a flexible mechanism for optimizing modulated reflectance measurement system 300/400 to analyze a range of different samples types. This is particularly true where a range of different density or dosage levels must be measured for different semiconductor wafers. It is also beneficial when analyzing ultra shallow junctions and other semiconductor features.

What is claimed is:

1. A measurement system for evaluating a sample, the device comprising:
   a series of illumination modules, each illumination module including a pump laser producing an intensity modulated output and a probe laser producing a non-modulated output, the pump and probe laser in each module chosen to optimize operation of the measurement system over a particular implantation dosage range;
   one or more optical elements positioned to selectively combine the outputs of the illumination modules into a collinear beam;
   an objective lens positioned to focus the collinear beam on the surface of the sample, the objective lens also gathering a portion of the collinear beam that is reflected by the periodically excited region;
   a detector for monitoring the reflected portion of the collinear beam and generating corresponding output signals; and
   a processor for evaluating the sample by analyzing the detector output signals.

2. A measurement system as recited in claim 1, where the series of illumination modules includes separate modules for high, medium and low implantation dosage ranges as well as an overall module that spans the combined range of the high, medium and low modules.

3. A measurement system as recited in claim 1, in which the illumination modules may be operated in any combination.

4. A method for evaluating a sample, the method comprising:
   selecting one or more illumination modules within a series of illumination modules, where each illumination module includes a pump laser producing an intensity modulated output and a probe laser producing a non-modulated output, the pump and probe laser in each module chosen to optimize measurement within a particular implantation dosage range;
   combining the illumination module outputs into a collinear beam;
   focusing the collinear beam on the surface of the sample to periodically excite a region of the sample surface;
   gathering a portion of the collinear beam that is reflected by the periodically excited region;
   monitoring the reflected portion of the collinear beam and generating corresponding output signals; and
   evaluating the sample by analyzing the detector output signals.

5. A method as recited in claim 4, wherein the series of illumination modules includes separate modules for high, medium and low implantation dosage ranges as well as an overall module that spans the combined range of the high, medium and low modules.

6. A method as recited in claim 4, in which the illumination modules may be selected in any combination.

7. An apparatus for evaluating a sample comprising:
   a first laser for generating a first pump beam of intensity-modulated radiation;
   a second laser for generating a second pump beam of intensity-modulated radiation;
   a third laser for generating a probe beam of non-modulated radiation;
   optical elements for focusing the first and second pump beams and the probe beam onto the sample;
   a detector for monitoring the reflected portion of the probe beam and generating output signals in response thereto that correspond to the modulated optical reflectivity of the sample; and
   a processor for evaluating the sample by analyzing the detector output signals.

8. An apparatus as recited in claim 7, wherein each of the first and second pump beams has a different frequency of modulation.

9. A measurement system as recited in claim 7, wherein the optical elements include one or more optical fibers.

10. A measurement system as recited in claim 7, wherein at least one of the optical elements is positioned to combine the first and second pump beams and the probe beam into a collinear beam.

11. A measurement system as recited in claim 10, wherein at least one of the optical elements is positioned to gather a portion of the collinear beam that is reflected by the sample.

12. A method for evaluating a sample, the method comprising:
   providing first and second pump radiation sources, each pump radiation source operable to produce an intensity-modulated pump beam;
   providing a probe radiation source operable to produce a non-modulated probe beam;
   combining the pump beams and the probe beam into a collinear beam;
   focusing the collinear beam on the surface of the sample to periodically excite a region of the sample surface;
   gathering a portion of the collinear beam that is reflected by the periodically excited region;
   monitoring the reflected portion of the collinear beam and generating corresponding output signals in response thereto that correspond to the modulated optical reflectivity of the sample; and
   evaluating the sample by analyzing the output signals.

13. A method as recited in claim 12, wherein each of the first and second pump radiation sources has a different frequency of modulation.

14. A method as recited in claim 12, wherein the probe radiation source produces a probe beam having a wavelength different than the respective wavelengths of the pump beams from the first and second pump radiation sources.

15. An apparatus for evaluating a sample comprising:
   a first laser for generating a pump beam of intensity-modulated radiation;
   a second laser for generating a first probe beam of non-modulated radiation at a first wavelength;
   a third laser for generating a second probe beam of non-modulated radiation at a second wavelength;
   optical elements for focusing the pump beam and the first and second probe beams onto the sample;
   a detector for monitoring the reflected portion of the first and second probe beams and generating output signals in response thereto that correspond to the modulated optical reflectivity of the sample; and
   a processor for evaluating the sample by analyzing the detector output signals.

16. A measurement system as recited in claim 15, wherein the optical elements include one or more optical fibers.

17. A measurement system as recited in claim 15, wherein at least one of the optical elements is positioned to combine the pump beam and first and second probe beams into a collinear beam.

18. A method for evaluating a sample, the method comprising:
providing a pump radiation source operable to produce an intensity-modulated pump beam;
providing first and second probe radiation sources each operable to produce a non-modulated probe beam at a different wavelength;
combining the pump beam and the first and second probe beams into a collinear beam;
focusing the collinear beam on the surface of the sample to periodically excite a region of the sample surface;
gathering a portion of the collinear beam that is reflected by the periodically excited region;
monitoring the reflected portion of the collinear beam and generating corresponding output signals in response thereto that correspond to the modulated optical reflectivity of the sample; and
evaluating the sample by analyzing the output signals.

* * * * *